(12) United States Patent
Ostgaard et al.

(10) Patent No.: US 7,579,190 B2
(45) Date of Patent: *Aug. 25, 2009

(54) METHOD AND APPARATUS FOR PREPARING CYTOLOGICAL SPECIMENS

(75) Inventors: Roy A. Ostgaard, Bolton, MA (US); Theodore S. Geiselman, Bolton, MA (US)

(73) Assignee: CYTYC Corporation, Marlborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/421,549

(22) Filed: Apr. 22, 2003

(65) Prior Publication Data

US 2003/0207456 A1    Nov. 6, 2003

Related U.S. Application Data

(63) Continuation of application No. 09/521,531, filed on Mar. 8, 2000, now Pat. No. 6,562,299, which is a continuation-in-part of application No. 09/520,421, filed on Mar. 8, 2000, now Pat. No. 6,572,824, and a continuation-in-part of application No. 09/156,952, filed on Sep. 18, 1998.

(51) Int. Cl.
*G01N 33/00* (2006.01)

(52) U.S. Cl. .............. 436/43; 436/518; 436/46; 436/47; 436/48; 436/49; 422/63; 422/65; 422/67

(58) Field of Classification Search .............. 436/518, 436/43, 46–49, 177; 422/63, 65, 67, 73, 422/100, 101; 435/287.1, 287.3, 287.7, 288.8
See application file for complete search history.

(56) References Cited

U.S. PATENT DOCUMENTS

| 4,224,032 | A | 9/1980 | Glover et al. |
|---|---|---|---|
| 4,224,277 | A | 9/1980 | Macho et al. |
| 4,234,539 | A | 11/1980 | Ginsberg et al. |
| 4,395,493 | A | 7/1983 | Zahniser et al. |
| 4,430,299 | A | 2/1984 | Horne |
| 4,705,630 | A | 11/1987 | Gordon et al. |
| 4,855,110 | A | 8/1989 | Marker et al. |
| 4,874,582 | A | 10/1989 | Gordon et al. |
| 5,039,615 | A | 8/1991 | Takahata |
| 5,075,079 | A | 12/1991 | Kerr et al. |

(Continued)

FOREIGN PATENT DOCUMENTS

EP    417 006 A2    3/1991

(Continued)

*Primary Examiner*—Sam P Siefke
(74) *Attorney, Agent, or Firm*—Vista IP Law Group LLP

(57) ABSTRACT

An automated system for preparing a plurality of cytological specimens from a plurality of fluid samples in vials includes an apparatus for collecting a monolayer of cells from each sample and transferring the cells to a microscope slide for fixing, staining, and inspection. The system includes a first loading station for receiving the sample vials, a second loading station for receiving consumables such as filter membranes, a slide dispenser, and an unloading area for removing completed specimen slides. To maintain one-to-one correlation between the samples and specimens produced therefrom, the system includes a subsystem for identifying each sample and permanently marking each slide with corresponding indicia prior to transferring the specimen thereto.

28 Claims, 9 Drawing Sheets

U.S. PATENT DOCUMENTS

| | | | |
|---|---|---|---|
| 5,081,038 A | 1/1992 | Sugaya et al. |
| 5,089,229 A | 2/1992 | Heidt et al. |
| 5,094,816 A | 3/1992 | Ishizaka et al. |
| 5,143,627 A | 9/1992 | Lapidus et al. |
| 5,151,184 A | 9/1992 | Ferkany |
| 5,164,575 A | 11/1992 | Neeley et al. |
| 5,209,903 A | 5/1993 | Kanamori et al. |
| 5,240,606 A | 8/1993 | Lapidus et al. |
| 5,262,049 A | 11/1993 | Ferkany |
| 5,269,918 A | 12/1993 | Lapidus et al. |
| 5,273,905 A | 12/1993 | Muller et al. |
| 5,282,978 A | 2/1994 | Polk, Jr. et al. |
| 5,336,467 A | 8/1994 | Heidt et al. |
| 5,356,595 A | 10/1994 | Kanamori et al. |
| 5,374,395 A | 12/1994 | Robinson et al. |
| 5,429,803 A | 7/1995 | Guirguis |
| 5,439,649 A | 8/1995 | Tseung et al. |
| 5,460,778 A | 10/1995 | Macindoe, Jr. |
| 5,460,968 A | 10/1995 | Yoshida et al. |
| 5,518,688 A | 5/1996 | Gianino |
| 5,589,400 A | 12/1996 | Hayes |
| 5,595,707 A | 1/1997 | Copeland et al. |
| 5,650,327 A | 7/1997 | Copeland et al. |
| 5,654,199 A | 8/1997 | Copeland et al. |
| 5,654,200 A | 8/1997 | Copeland et al. |
| 5,670,329 A | 9/1997 | Oberhardt |
| 5,676,910 A | 10/1997 | Levine et al. |
| 5,690,815 A | 11/1997 | Krasnoff et al. |
| 5,854,075 A | 12/1998 | Levine et al. |
| 5,879,944 A | 3/1999 | Komatsu |
| 5,981,166 A | 11/1999 | Mandecki |
| 6,106,781 A * | 8/2000 | Rosenberg ............... 422/64 |
| 6,309,362 B1 | 10/2001 | Guirguis |
| 6,319,470 B1 | 11/2001 | Lefevre et al. |
| 6,562,299 B1 * | 5/2003 | Ostgaard et al. ........... 422/65 |
| 6,572,824 B1 * | 6/2003 | Ostgaard et al. ........... 422/67 |
| 2003/0207455 A1 * | 11/2003 | Ostgaard et al. ........... 436/43 |

FOREIGN PATENT DOCUMENTS

| | | |
|---|---|---|
| EP | 0 508 568 A2 | 10/1992 |
| EP | 0 740 142 A2 | 10/1996 |
| EP | 0 984 263 A1 | 3/2000 |
| WO | WO 99/10723 | 3/1999 |
| WO | WO 99/49295 | 9/1999 |
| WO | WO 00/62035 | 10/2000 |

* cited by examiner

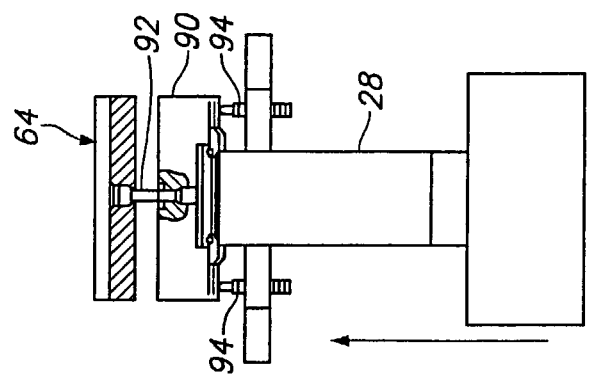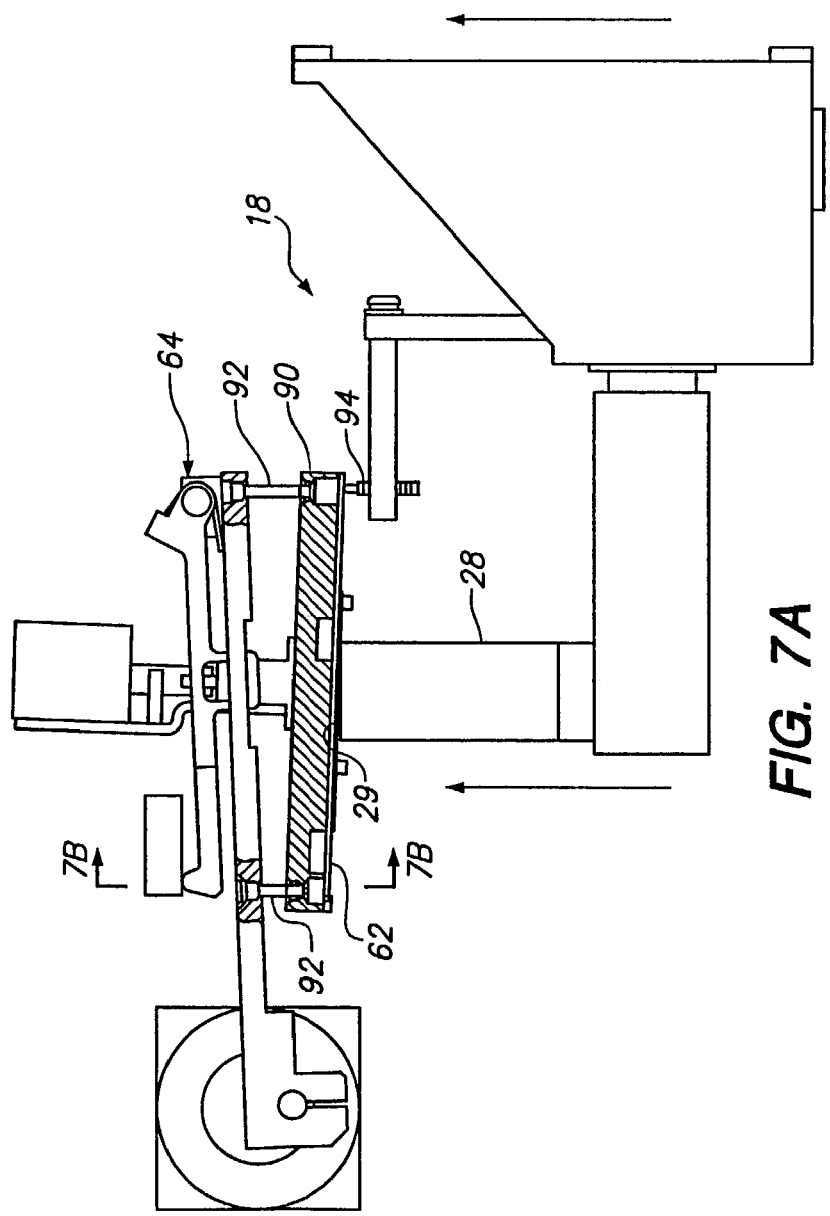

METHOD AND APPARATUS FOR PREPARING CYTOLOGICAL SPECIMENS

RELATED APPLICATIONS

This application is a Continuation of U.S. application Ser. No. 09/521,531 filed Mar. 8, 2000, now U.S. Pat. No. 6,562,299 which is a continuation-in-part of U.S. patent application Ser. No. 09/156,952 filed Sep. 18, 1998, entitled "Sample Vial for Use in Preparing Cytological Specimen", and a continuation-in-part of U.S. application Ser. No. 09/520,421 filed Mar. 8, 2000, now U.S. Pat. No. 6,572,824, the disclosure of which is herein incorporated by reference in its entirety.

TECHNICAL FIELD

The present invention relates to preparation of cytological specimens and, more specifically, to an automated method and apparatus for preparing a plurality of cytological specimens from a common number of patient samples and maintaining one-to-one correlation between the patient samples and the specimens.

BACKGROUND

Cytology is a branch of biology dealing with the study of the formation, structure, and function of cells. As applied in a laboratory setting, cytologists, cytotechnologists, and other medical professionals make medical diagnoses of a patient's condition based on visual examination of a specimen of the patient's cells. A typical cytological technique is a "pap smear" test, in which cells are scraped from a woman's cervix and analyzed in order to detect the presence of abnormal cells, a precursor to the onset of cervical cancer. Cytological techniques are also used to detect abnormal cells and disease in other parts of the human body.

Cytological techniques are widely employed because collection of cell samples for analysis is generally less invasive than traditional surgical pathological procedures such as biopsies, whereby a tissue specimen is excised from the patient using specialized biopsy needles having spring loaded translatable stylets, fixed cannulae, and the like. Cell samples may be obtained from the patient by a variety of techniques including, for example, by scraping or swabbing an area, or by using a needle to aspirate body fluids from the chest cavity, bladder, spinal canal, or other appropriate area. The cell samples are placed in solution and subsequently collected and transferred to a glass slide for viewing under magnification. Fixative and staining solutions may be applied to the cells on the glass slide for preserving the specimen for archival purposes and for facilitating examination.

It is generally desirable that the cells on the slide have a proper spatial distribution, so that individual cells can be examined. A single layer of cells is typically preferred. Accordingly, preparing a specimen from a fluid sample containing many cells typically requires that the cells first be separated from each other by mechanical dispersion, fluidic shear, or other techniques so that a thin, monolayer of cells can be collected and deposited on the slide. In this manner, the cytotechnologist can more readily discern abnormal cells. The cells are also able to be counted to ensure that an adequate number of cells have been evaluated.

Certain methods and apparatus for generating a thin monolayer of cells on a slide advantageous for visual examination are disclosed in U.S. Pat. No. 5,143,627 issued to Lapidus et al. and entitled "Method and Apparatus for Preparing Cells for Examination;" U.S. Pat. No. 5,240,606 issued to Lapidus et al. and entitled "Apparatus for Preparing Cells for Examination;" U.S. Pat. No. 5,269,918 issued to Lapidus et al. and entitled "Clinical Cartridge Apparatus;" and U.S. Pat. No. 5,282,978 issued to Polk, Jr. et al. and entitled "Specimen Processor Method and Apparatus," all of which are assigned to the assignee of the present invention and all of the disclosures of which are incorporated herein by reference in their entirety.

According to one method disclosed in these patents, a patient's cells in a preservative fluid in a sample container are dispersed using a spinning sample collector disposed therein. A controlled vacuum is applied to the sample collector to draw the fluid through a screen filter thereof until a desired quantity and spatial distribution of cells is collected against the filter. Thereafter, the sample collector is removed from the sample container and the filter portion impressed against a glass slide to transfer the collected cells to the slide in substantially the same spatial distribution as collected.

While apparatus manufactured according to the teachings of one or more of these patents have been commercially successful, such as the ThinPrep® 2000 System manufactured and sold by Cytyc Corporation located in Boxborough, Mass., such apparatus requires substantially constant attendance by a trained operator. For example, for each specimen to be prepared, the operator must load the system with an open sample vial containing the patient's cells in preservative fluid, a sample collector with filter, a glass slide, and an open fixative bath vial containing a fixative solution. The system then cycles automatically, the cells being dispersed by the sample collector, collected against the filter, and transferred to the slide. The slide is then automatically deposited in the fixative bath vial where it must be retrieved by the operator for manual loading in a staining rack for further processing. Thereafter, the sample vial and sample collector must be removed from the system, to avoid inter-sample contamination, before replacements and a new slide are installed to produce another specimen from a different patient's sample.

Once a specimen is prepared, fixed, and stained, the specimen may be manually visually inspected by a cytotechnologist, typically under magnification, and with or without various sources of illumination. Alternatively or additionally, automated machine vision systems have been adapted to aid cytological inspection. For example, an automated vision system may perform a preliminary assessment of the entire slide on which the specimen is disposed to alert the cytotechnologist to potentially the most relevant areas of the slide for close inspection, or may be used to rescreen specimens already analyzed by the cytotechnologist.

SUMMARY OF THE INVENTION

While automated specimen preparation systems such as those described hereinabove perform as designed, it is desirable to further reduce manual intervention required of a system operator so as to increase system throughput and operating efficiency. Accordingly, it is desirable to provide the capability wherein a plurality of sample vials, sample collectors with filters, and inspection media such as, for example, glass slides may be loaded in the system. The system then cycles automatically until all of the sample vials are processed and respective specimen slides produced. As a result, after initial loading, the system can operate unattended.

In one embodiment of the invention, a system includes a sample vial tray for loading of a plurality of closed, capped sample vials. The vials include particles of interest, such as cells, tissue samples, assay product, or other material, typically dispersed in a fluid medium. A sample vial transfer assembly serially retrieves each sample vial, unscrewing a cap thereof, and positioning the now open vial in a position for cooperation with a sample collector and filter, which may be drawn automatically from another tray having a plurality of sample collectors. A sample collector or other mechanism prepares the sample for collection such as, for example, by agitating the sample in a manner so as to create a generally uniform dispersion of particles of interest throughout the sample. Once the particles cells are dispersed, collected against the filter, and transferred to a slide drawn automatically from a slide dispenser having a plurality of clean slides stored therein, the slide is then automatically deposited in a fixative bath vial for a period sufficient to fix the specimen on the slide. Alternatively, the fixative solution may be applied directly to the specimen on the slide by spraying with an air brush or similar technique. In either case, the slide may then be transferred to one of a number of multi-position staining racks previously loaded in the system, so that the fixative solution may dry. Once a first patient's specimen is prepared, the open sample vial is recapped and replaced in the sample vial tray. The filter of the sample collector may be breached to prevent reuse and resultant inter-sample contamination. The next sample vial can then be retrieved and the specimen preparation method repeated until all of the sample vials are processed. Accordingly, once the system operator loads the sample vial tray, sample collector tray, slide dispenser, and staining racks, and initiates the automatic sequence, the system can operate unattended.

In order to maintain the integrity of the specimens so produced, it is desirable to maintain one-to-one correlation between the contents of the sample vials and the respective specimens produced therefrom. When a cell sample is collected from a patient and deposited in the preservative fluid in the sample vial, creating cellular particles in a liquid suspension, the vial may be marked with unique identifying indicia corresponding to the type of sample, patient, date obtained, etc. In one embodiment, the identifying indicia may be a bar code label. When the sample vial is loaded into the system and retrieved from the sample vial tray by the sample vial transfer assembly, the indicia corresponding to the sample is identified. In the case of a bar code, a laser bar code scanner can be used.

Next, an analytical element, such as a microscope slide, is marked with indicia corresponding to the sample indicia. In one embodiment, the analytical element is marked with ink transferred thereto by a printer. The ink may be transferred to multiple overlapping locations, spatially offset from each other on the analytical element, to improve the readability of the element indicia.

The element indicia are then read automatically by the system. In the case where the element indicia are man-readable alphanumeric characters, an optical character recognition system can be employed in the reading step. Once the system verifies that the element indicia corresponds to the sample indicia, the cells in the sample vial are dispersed, collected, and transferred to the analytical element to produce the specimen. In one embodiment, the system collects a spatial distribution of the cellular particles from the liquid suspension and disposes the collected particles on a stratum of the analytical element or slide. The spatial distribution may be substantially a monolayer of cells collected on a filter or porous membrane of a sample collector. The filter or membrane of the sample collector may be breached mechanically, pneumatically, hydraulically, or otherwise in order to prevent reuse of the sample collector and resultant inter-sample contamination.

An apparatus according to the invention for processing a specimen from a fluid sample may include a processor, an identifier in communication with the processor for identifying indicia corresponding to the sample, a marker in communication with the processor for marking an analytical element with indicia corresponding to the sample indicia, and a reader in communication with the processor for reading the element indicia. Once the processor verifies that the element indicia corresponds to the sample indicia, a specimen transferrer in communication with the processor transfers a specimen from the sample to the analytical element.

BRIEF DESCRIPTION OF THE DRAWINGS

The invention, in accordance with preferred and exemplary embodiments, together with further advantages thereof, is more particularly described in the following detailed description taken in conjunction with the accompanying drawings in which:

FIG. 7A is a schematic side view of a pre-contact condition of a sample collector approaching a specimen slide;

FIG. 7B is a partial schematic cross-sectional view of the apparatus depicted in FIG. 7A taken along line 7B-7B.

DESCRIPTION

Figure 1:
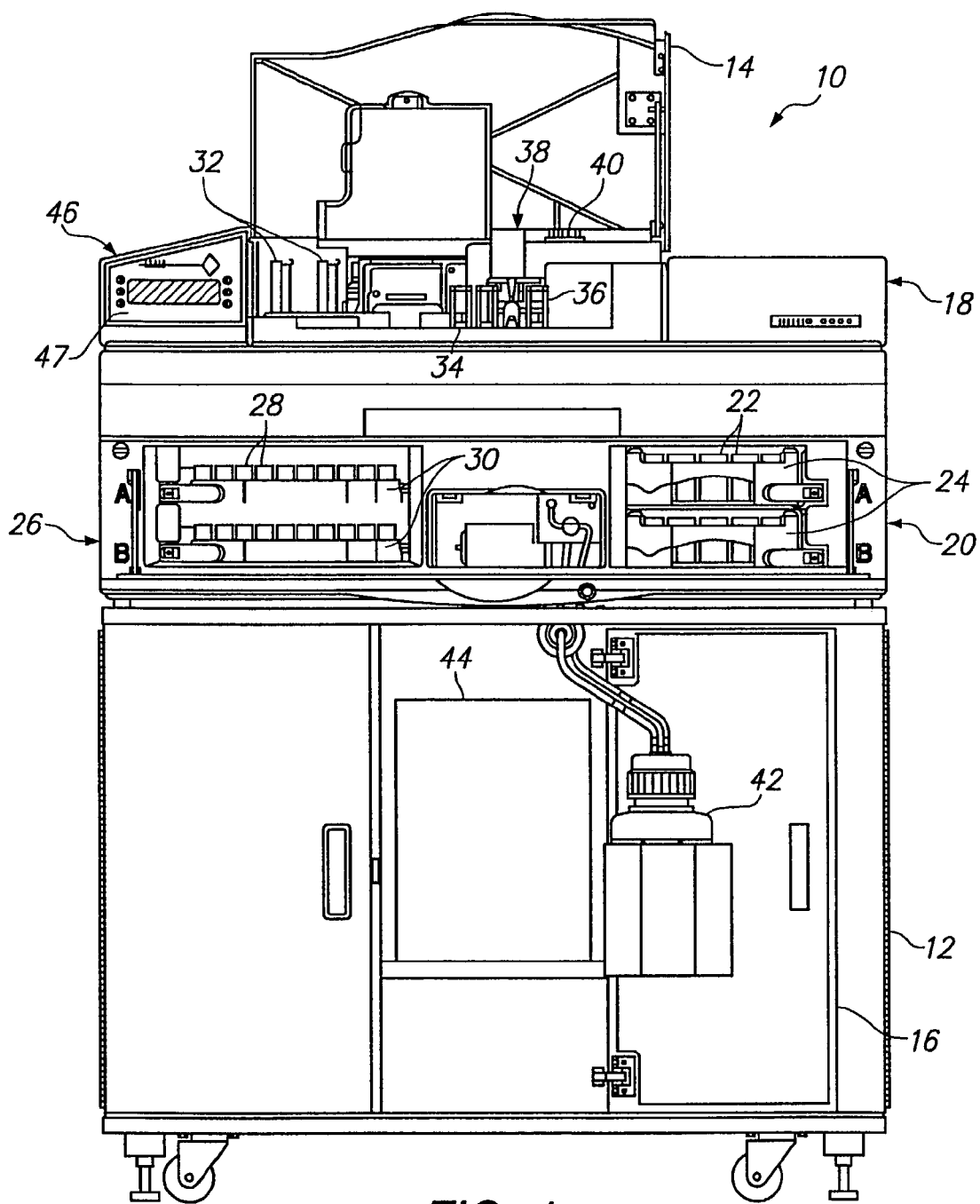
FIG. 1 is schematic front view of an automated specimen processing apparatus in accordance with one embodiment of the present invention.
Figure 2:
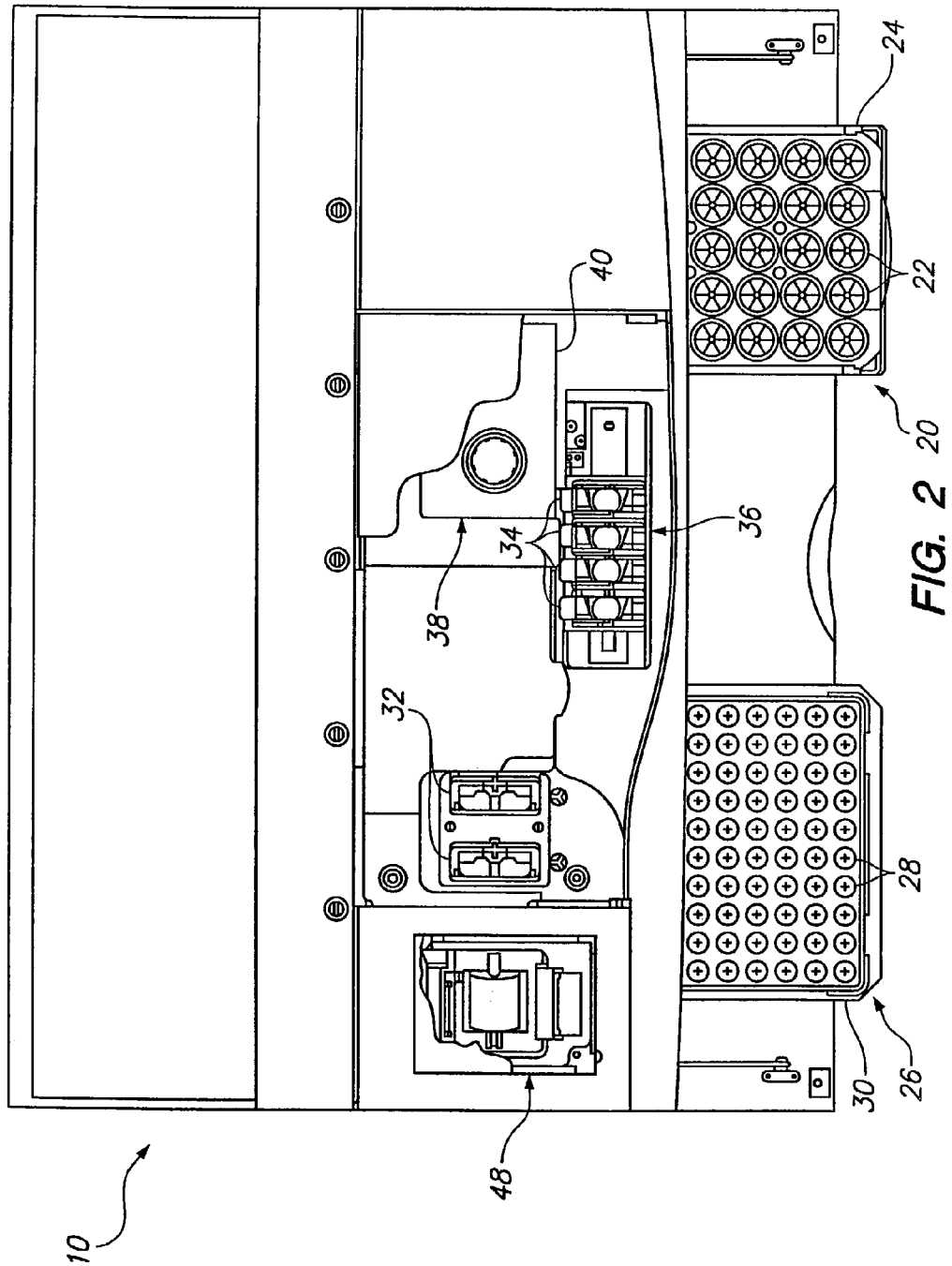
FIG. 2 is a schematic top plan view of the specimen processing apparatus depicted in FIG. 1.

FIGS. 1 and 2 are schematic front and top plan views of an automated specimen preparing system 10 for preparing a plurality of specimens from a plurality of fluid samples. The system 10 may be mounted on a wheeled instrument cart 12 for portability. Depicted with an upper cover 14 and front door 16 in open positions, the system 10 includes a specimen preparing apparatus 18 or transferrer, functionally of the type disclosed in the aforementioned patents subject to improvements discussed further hereinbelow. Namely, the specimen preparing apparatus 18 includes subassemblies for automatically dispersing, collecting, and transferring a monolayer of cells to an analytical element, such as a microscope slide. The particular structural details of the specimen preparing apparatus 18, however, may vary from those disclosed in the aforementioned patents.

Figure 5:
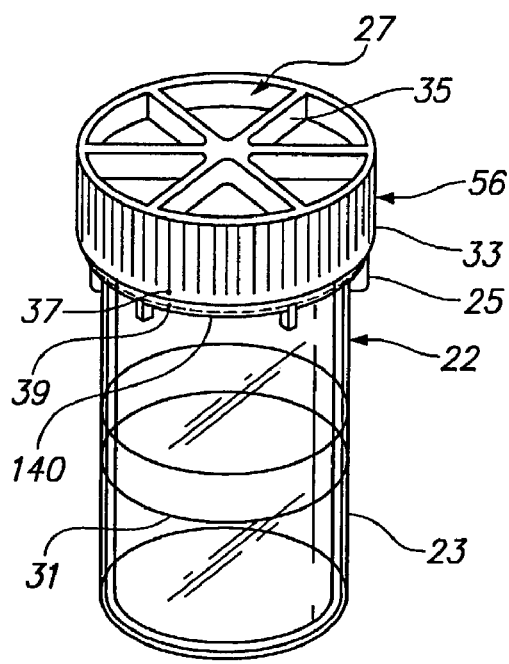
FIG. 5 is a schematic perspective view of a capped sample vial in accordance with one embodiment of the present invention.

The system 10 includes a first loading station 20 for receiving a plurality of patient samples, each disposed in a sample vial 22, as best seen in FIG. 5. As depicted, the sample vial loading station 20 may have more than one tier to accommodate multiple sample vial trays 24, two trays 24 being shown. Each tray 24 is removable to facilitate handling and preloading of the vials 22. In one embodiment, each tray 24 may include locations for forty samples vials 22, providing a system 10 that can automatically process up to eighty samples without operator intervention. For a system 10 with a process cycle time of about ninety seconds per sample, eighty samples can be processed in about two hours of continuous, unattended operation.

Figure 6:
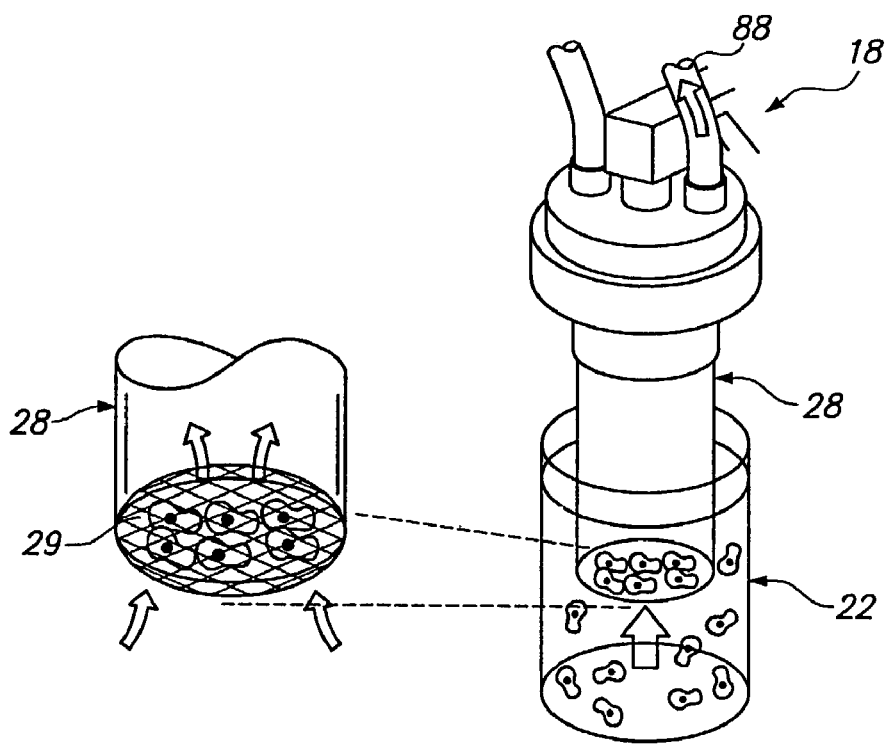
FIG. 6 is a schematic perspective view of a sample collector during cell collection in accordance with one embodiment of the present invention.

The system 10 also includes a second loading station 26 for receiving a plurality of sample collectors 28 disposed in a sample collector tray 30. As best seen in FIG. 6, each sample collector 28 has a porous membrane or filter 29 at one end thereof against which cells are collected. The sample collector loading station 26 may have more than one tier to accommodate multiple sample collector trays 30, two trays 30 being shown. Each tray 30 is removable to facilitate handling and preloading of the sample collectors 28. In one embodiment, each tray 20 may include locations for one hundred sample collectors 28, providing a system 10 which can automatically process the eighty samples without operator intervention. The collectors 28 may also be provided to the operator preloaded in the collector tray 30, which may be reusable or discardable, as desired. Both loading stations 20, 26 include elevators for raising and lowering the trays 24, 20, as required, so that sample vial and collector transfer assemblies can access, respectively, each of the sample vials 22 and collectors 28.

Blank glass microscope slides are preloaded in two removable cartridges 32, each with the capacity to hold one hundred slides. Two cartridges 32 are provided to ensure that there are a sufficient number of slides available in the system 10 to process the maximum number of sample vials 22. While glass microscope slides are typically used for preparing cytological specimens, other analytical elements, such as natural or synthetic material assay strips and the like, are suitable for other analyses and testing, as known by those skilled in the art, and could be employed in the system 10 with suitable handling equipment.

One or more staining racks 34 may be provided in an unloading area 36 of the system 10 to receive the slides once the cytological specimens have been transferred thereto. In the depicted embodiment, four staining racks 34 are provided, each with a capacity of twenty slides. Accordingly, eighty sample vials 22 can be processed without having to remove the staining racks 34. Staining rack adaptors may be provided so that the staining racks 34 can be loaded into automated, commercially available cytological specimen stainers after removal from the system 10. Accordingly, prepared specimens can be efficiently and rapidly unloaded from the system 10 and the specimens stained with minimal manual intervention.

Once a specimen has been transferred to a slide and before the slide is disposed in the staining rack 34, a fixative solution may be applied to the specimen at a coating station 38. The coating station 38 includes a fixative reservoir 40 which holds the solution used to fix or preserve the specimen on the slide after preparation by the system 10. In one embodiment, the reservoir has sufficient capacity to allow at least a day and preferably a week of average usage without the need for refilling or replacement. The fixative may be applied to the specimen by an air brush technique in which the fixative solution is gently sprayed on the specimen so as not to disturb the spatial distribution of the cells on the slide.

More specifically, in one embodiment, an airbrush having a generally conical spray distribution pattern may be used to apply a substantially uniformly dense layer of fixative solution to a generally circular cell transfer area on the slide. A fine mist may be applied in one or more short duration bursts to prevent displacing a monolayer of cells on the slide, typically using a very small volume of fluid dispensed from the airbrush using very low differential air pressure. For example, each burst may apply about 20±2 µl of fixitive solution over a period of about 0.6 seconds. A slight positive pressure may be maintained in the reservoir 40 to compensate for any pressure head, thereby maintaining control of the dispensed volume per burst. The airbrush may be of any conventional design capable of handling the small volumes applied and capable of providing the desired uniform conical spray distribution pattern. In general, primarily an airbrush nozzle, needle valve, and body are employed, with flow being controlled by an external valve, rather than a trigger valve typically supplied with the airbrush. The pressure source applied to the airbrush may be calibrated and maintained at a fixed pressure in order to ensure a predetermined fixative flow rate for a particular airbrush, thereby achieving the desired dispensed volume per burst.

During preparation of each specimen, a small volume of preservative fluid from the sample vial 22 is drawn through the collector membrane 29. A waste bottle 42 is provided in fluidic communication with the specimen preparing apparatus 18 so that waste fluid can be drained during specimen preparation. The waste bottle 42 may be mounted to an interior of the front door 16 to facilitate removal and replacement of the bottle 42 for emptying.

A waste bin 44 may also be provided to catch used sample collectors 28. Prior to being discarded, the porous membrane or filter 29 of each collector 28 may be breached so that the collector 28 cannot be reused and possibly contaminate another specimen. The membrane 29 may be breached by any of a variety of methods. For example, the collector 28 may be overpressurized, pneumatically with air or hydraulically with fluid, so as to burst the membrane. Alternatively, the membrane 29 can be mechanically ruptured, for example, by impressing the membrane 29 on a sharp object, such as a pointed protrusion or knife edge mounted in the system 10. For preparing cytological specimens, the membrane may have a pore size on the order of about ten microns or less.

A computer controller or processor 46 is provided to communicate with and coordinate operation of the various sensors and components of the system 10 to permit automatic, unattended operation during specimen preparation. The processor 46 includes an appropriate operator interface 47 with associated input keypad or buttons and an output display, such as a liquid crystal diode display. Instructions, prompts, and error messages may be in text, error code, or symbol formats. Text displays may be in a variety of operator selectable languages, such as English, French, German, Italian, Japanese, and Spanish. Audible outputs corresponding to operator prompts, error conditions, keypad inputs, and completion of automatic processing may be provided. A thermal paper printer 48 or other type of printer may be provided, as well, to generate a permanent paper record of system operation and sample processing. For example, for each batch of eighty or fewer sample vials 22 processed, the printer 48 may generate a report containing the date and time processing began, a listing of the sample vials 22 not successfully processed (including error type and tray location), and a listing of the sample vials 22 successfully processed (including sample identification information and tray location).

Figure 3:
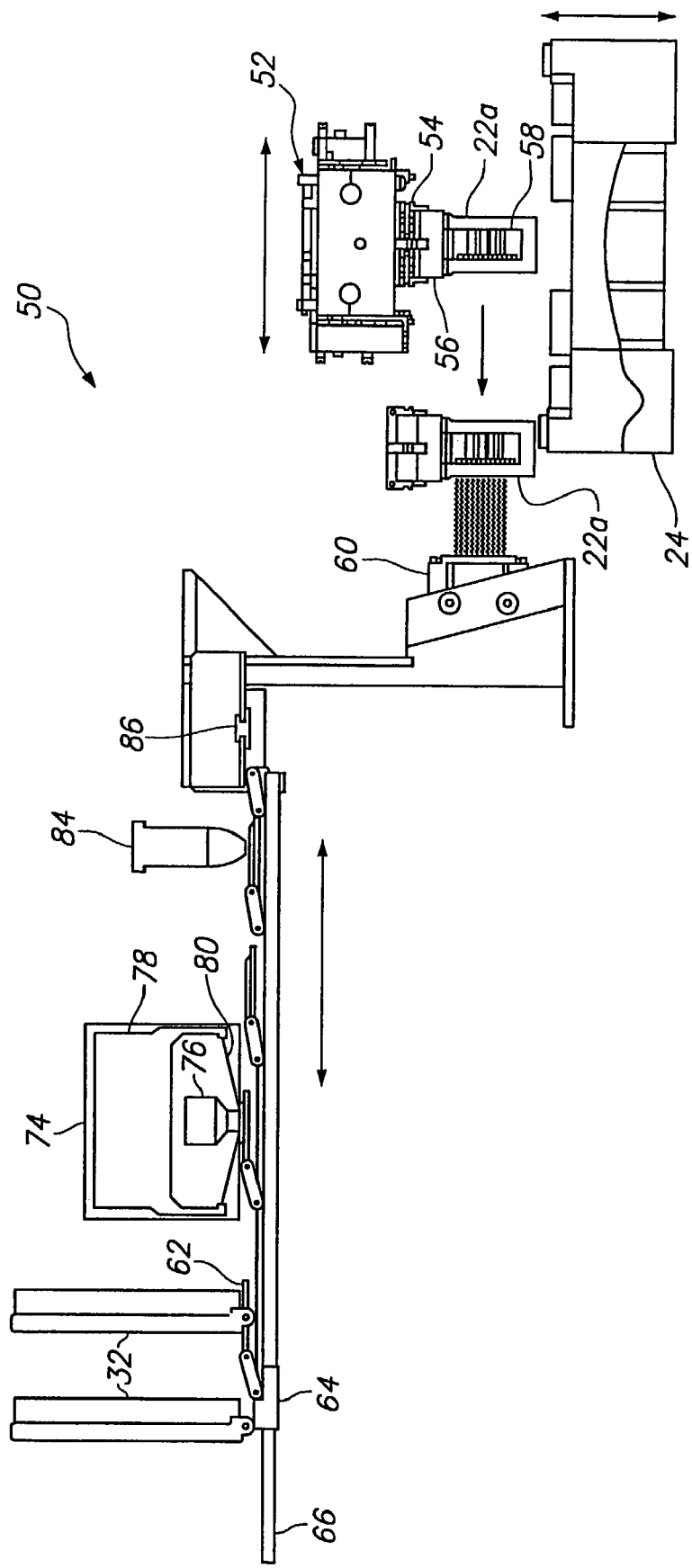
FIG. 3 is a schematic front view of an identification correlation subsystem of a specimen processing apparatus in accordance with one embodiment of the present invention.
Figure 4:
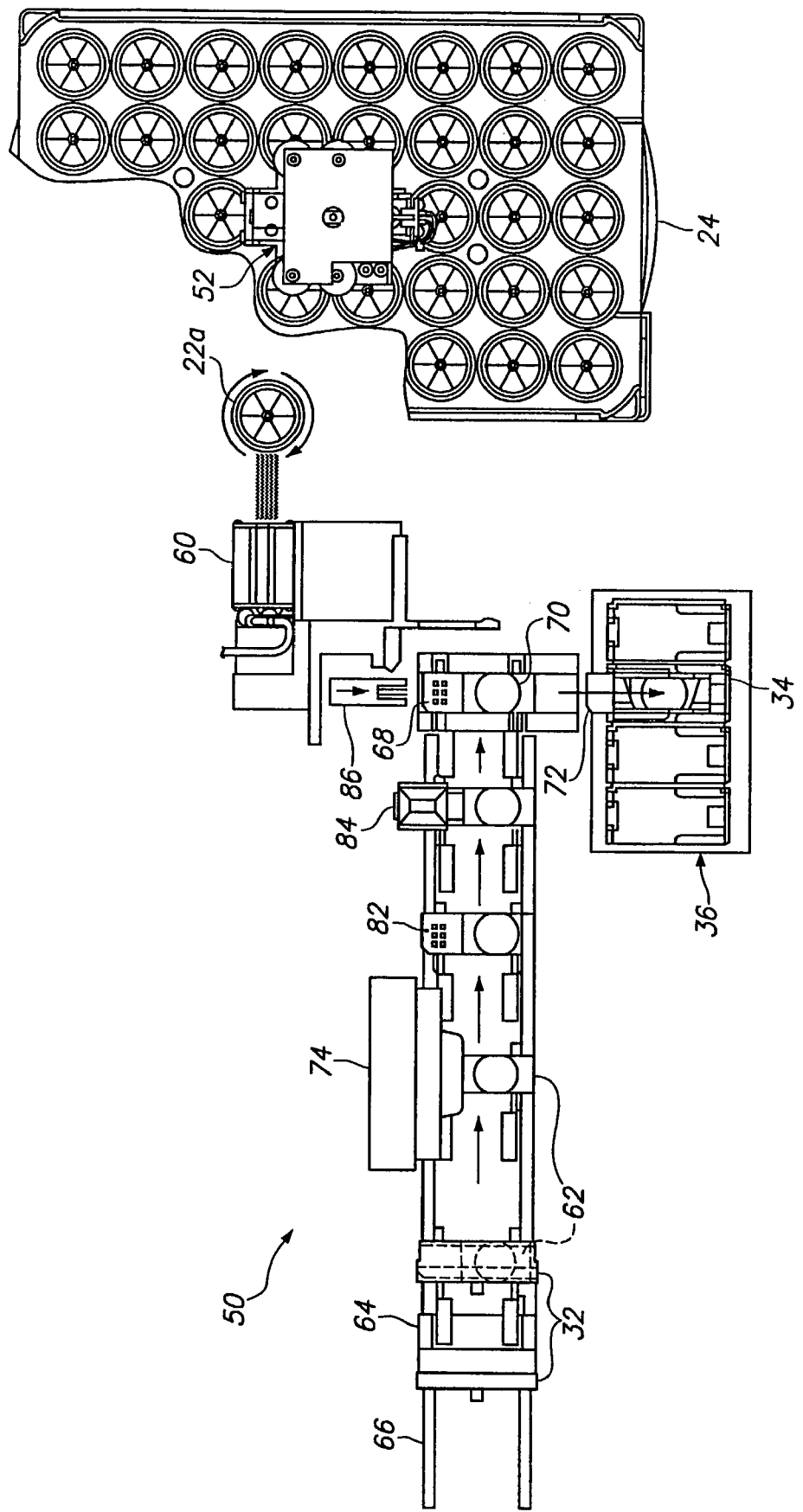
FIG. 4 is a schematic top plan view of the identification correlation subsystem of a specimen processing apparatus depicted in FIG. 3.

In order that the system 10 maintains correlation between each sample vial 22 and a respective specimen prepared therefrom, an identification correlation subsystem 50 is provided, as depicted schematically in front and top plan views in FIGS. 3 and 4, respectively. In accordance with one embodiment of the present invention, in order to prepare a specimen from a sample vial 22, a selected capped vial 22a is removed from one of the sample vial trays 24 by a sample vial transfer assembly 52. The vial transfer assembly 52 includes a four-fingered gripper 54 configured to reliably and repeatable grasp a cap 56 of the vial 22a. The vial transfer assembly 52 is movable about a plane above the vial tray 24, left to right and into and out of the drawing as depicted in FIG. 3, so that the gripper 54 can be aligned above any of the forty vials 22 loaded in the tray 24. Once aligned with a desired vial 22a, the tray 24 is raised by the tray elevator, the vial cap 56 grasped by the gripper 54 and tightened as will be discussed in greater detail hereinbelow, and the tray 24 lowered. In order to access vials 22 on the other tray 24, the vial transfer assembly 52 can be retracted to one side, outside a footprint of the trays 24 and the tray elevator operated to raise or lower the tray 24, as necessary. Similar handling is provided for the sample collectors 28 and collector trays 30.

Each vial 22 includes identifying indicia, such as a bar code label 58 mounted thereon, which corresponds to and uniquely identifies the vial 22 and the sample contained therein. The selected vial 22a is then presented by the vial transfer assembly 52 to an identifier, such as a laser scanner bar code reader 60, so that the particular vial 22a can be identified. Because the circumferential orientation of the vials 22 in each tray 24 and that of the respective bar code labels 58 can vary, upon presentation to the bar code reader 60, the vial transfer assembly 52 rotates the sample vial 22a about a vertical axis passing generally through an axial centerline thereof, as best seen in FIG. 4, to present the label 58 to the reader 60.

Once the bar code label 58 or other identifying indicia has been identified and communicated to the processor 46, the processor 46 directs the preparation of an analytical element, such as a microscope slide 62, for receipt of a specimen from the selected vial 22a.

Referring to FIG. 4, a slide carriage 64, translatable along a carriage rail 66, first extracts a slide 62 from one of the slide cartridges 32. Each slide 62 has tightly toleranced dimensions and chamfered edges to facilitate handling and transfer of the slide 62 by the components of the system 10 and minimize the likelihood of mishandling or jamming. In one embodiment, the slide 62 is manufactured from glass and has a width of about one inch, a length of about three inches, and a thickness of about 0.04 inches. One end 68 of the slide 62 is frosted or coated to facilitate marking, as will be discussed in greater detail hereinbelow. The frosted end 68 may have an area of about one square inch. A frosted annulus 70, defining an area to where the cells are transferred, may also be provided to facilitate manual or automatic scanning of sparse specimens. The bounded specimen area may have an area of about one square inch, substantially equivalent to the surface area of the membrane 29. Additionally, one corner 72 of the frosted end 68 of each slide 62 may be chamfered to a greater degree than the other corners to ensure proper orientation of the slide 62 in the slide cartridge 32 and proper presentation of the slide 62 to downstream components.

Once the bar code label 58 on the sample vial 22a has been identified and before the sample vial 22a is uncapped and a specimen produced therefrom, the slide carriage 64 conveys the slide 62 to a marker in communication with the processor 46 for marking the slide 62 with indicia corresponding to the sample indicia on the bar code label 58. In one embodiment, the marker may be a printer 74, such as an ink jet printer, thermal printer, laser printer, or other suitable marker capable of producing substantially permanent indicia on the slide 62. In the depicted embodiment, the printer 74 is a dot matrix impact printer utilizing a multi-pin impact head 76 and replaceable ribbon cartridge 78, which feeds an ink ribbon 80 to a zone between the impact head 76 and the slide 62.

The processor 46 next directs the printer 74 to mark the slide 62. The slide indicia may have any of a variety of forms including one or more alphanumeric characters, as shown generally at 82. It is generally desirable to mark the slides 62 with man-readable indicia so that the cytologist examining a fixed, stained specimen can readily identify the specimen and associated sample from which the specimen was prepared. Further, specimens are often archived and retained for extended periods. Accordingly, it is generally desirable to avoid using an indicia standard that may fall into disuse or become obsolete. While the slide indicia may be marked on an adhesive label bonded to the slide 62, subsequent processing such as fixing and staining may degrade the indicia or bond. Because specimen slides 62 are often archived in slide file drawers, it is generally desirable that the slide indicia 82 be oriented along the width or narrow dimension of the frosted end 68 so as to be readable without requiring removal of the slide 62 from the file drawer.

The slide indicia printing method and printing media should be resistant to the solvents used in the specimen preparing, fixing, and staining processes. Typical solvents include ethanol, methanol, xylene, water, and a clarifier solution consisting of 0.025% glacial acetic acid in distilled water. In general, commercially available carbon black based printing ink ribbons 80 have been found to perform well when printing on frosted ends 68 produced by coating the ends of the slides 62 with a white epoxy paint material.

In order to generate readily discernible characters 82 using a low cost printer 74, the processor 46 may control operation of the printer 74 and the slide carriage 64 so as to first transfer a spot of ink to a first location on the slide 62 and then transfer another spot of ink to a second location offset spatially and slightly overlapping the first location. By double-striking, or alternatively striking a third or more times in different offset directions to blend the ink spots in a particular region of the character, a relatively low cost nine pin dot matrix printer can produce alphanumeric characters substantially visually consistent with those produced by a much more expensive dot matrix printer having many more pins in the impact head.

Once the slide 62 is marked, the processor 46 directs the slide carriage 64 to advance the slide 62 along the carriage rail 66 to a reader in communication with the processor 46 for reading the slide indicia 82. In the case where the specimen indicia is composed of alphanumeric characters, the reader may be an optical character recognition (OCR) scanner 84 or system. In one embodiment, a total of four strikes are employed per pin using a nine pin printer in order to meet OCR font specifications typical for higher resolution dot matrix printers.

The processor 46 verifies both that the slide indicia 82 is readable by the OCR scanner 84 and that the slide indicia 82 corresponds to the sample indicia identified from the bar code label 58 on the selected vial 22a. In the event the slide indicia 82 cannot be read or the slide indicia 82 does not correspond to the sample indicia, the slide 62 may be removed automatically from the slide carriage 64 using an ejector or other apparatus, as discussed in greater detail hereinbelow, and discarded in the waste bin 44 or other waste receiving area. If multiple slides 62 fail in succession or if more than a predetermined number of slides fail during processing of a batch of sample vials 22, the system 10 may be programmed optionally to halt automatic operation and alert the operator with a suitable error message.

Upon verification of both criteria, the sample vial transfer assembly 52 removes the cap 56 from the sample vial 22a so that the specimen preparing apparatus 18 can cycle. A sample collector 28 is taken automatically from the collector tray 30 at the second loading station 26 and inserted into the specimen preparing apparatus 18. Thereafter, the membrane 29 of the collector 28 is inserted into the specimen vial 22a to a predetermined depth as shown in FIG. 6 and, in one embodiment, the collector 28 is rotated to disperse the cells in the preservative fluid. A vacuum system 88 applies a controlled pressure and vacuum cycle to the collector 28 so that cells are collected in a monolayer against the membrane 29. The cells are subsequently transferred to the zone within the frosted annulus 70 on the slide 62 as shown schematically in FIGS. 7A-C. According to another embodiment, the sample vial 22 may be rotated prior to uncapping to disperse the cells in the preservative solution, as will be discussed in greater detail hereinbelow.

In order to provide for transfer of the collected cells to the slide 62 without disturbing the spatial distribution thereof, it is desirable that the membrane 29 of the collector 28 first contact the slide 62 generally at a single location, forming a predetermined small pre-contact angle between the substantially planar membrane 29 and a deposition surface of the slide 62, and then gently and gradually enter into complete contact with the slide 62.

As depicted in FIG. 7A, after collecting the cells on the membrane 29, the specimen preparing apparatus 18 inverts the collector 28 to drain any excess fluid therein into the waste bottle 42 mounted on the cart door 16. The apparatus 18 slowly elevates the membrane 29 to a position proximate the slide 62, which is retained in an inverted orientation in a slide holder 90 hanging from two studs 92 captured by the slide carriage 64. Insofar as the studs 92 are of different lengths, the holder 90 and the slide 62 are positioned in an orientation which is slightly offset from horizontal.

Figure 7C:
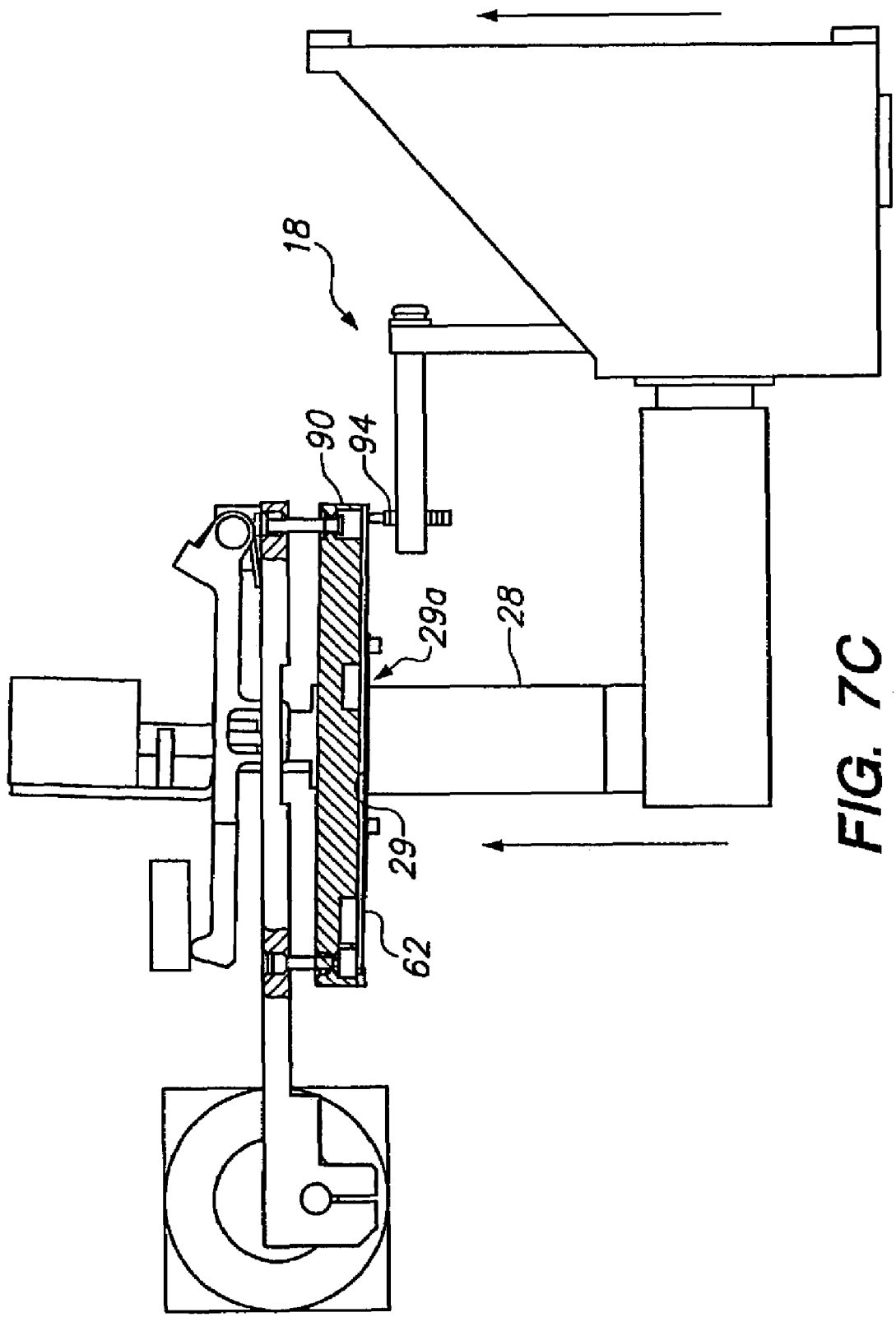
FIG. 7C is a schematic side view of an initial contact condition for a sample collector contacting a specimen slide.

FIG. 7B is a partial schematic cross-sectional view of the specimen preparing apparatus 18 and slide holder 90 depicted in FIG. 7A, taken along line 7B-7B. Viewed in conjunction with FIG. 7A, as the apparatus 18 continues to elevate the collector 28, two pre-adjusted jack screws 94 first contact the slide holder 90 at one end thereof. As the apparatus 18 elevates the collector 28 further, the holder 90 achieves a more horizontal orientation due to contact with the jack screws 94 until an edge of the membrane 29, shown generally at 29a in FIG. 7C, contacts the slide 62. At this point in the cycle, the angle formed between the membrane 29 and the slide 62 may be on the order of several degrees or less, typically 0.75±0.25 degrees.

Figure 7D:
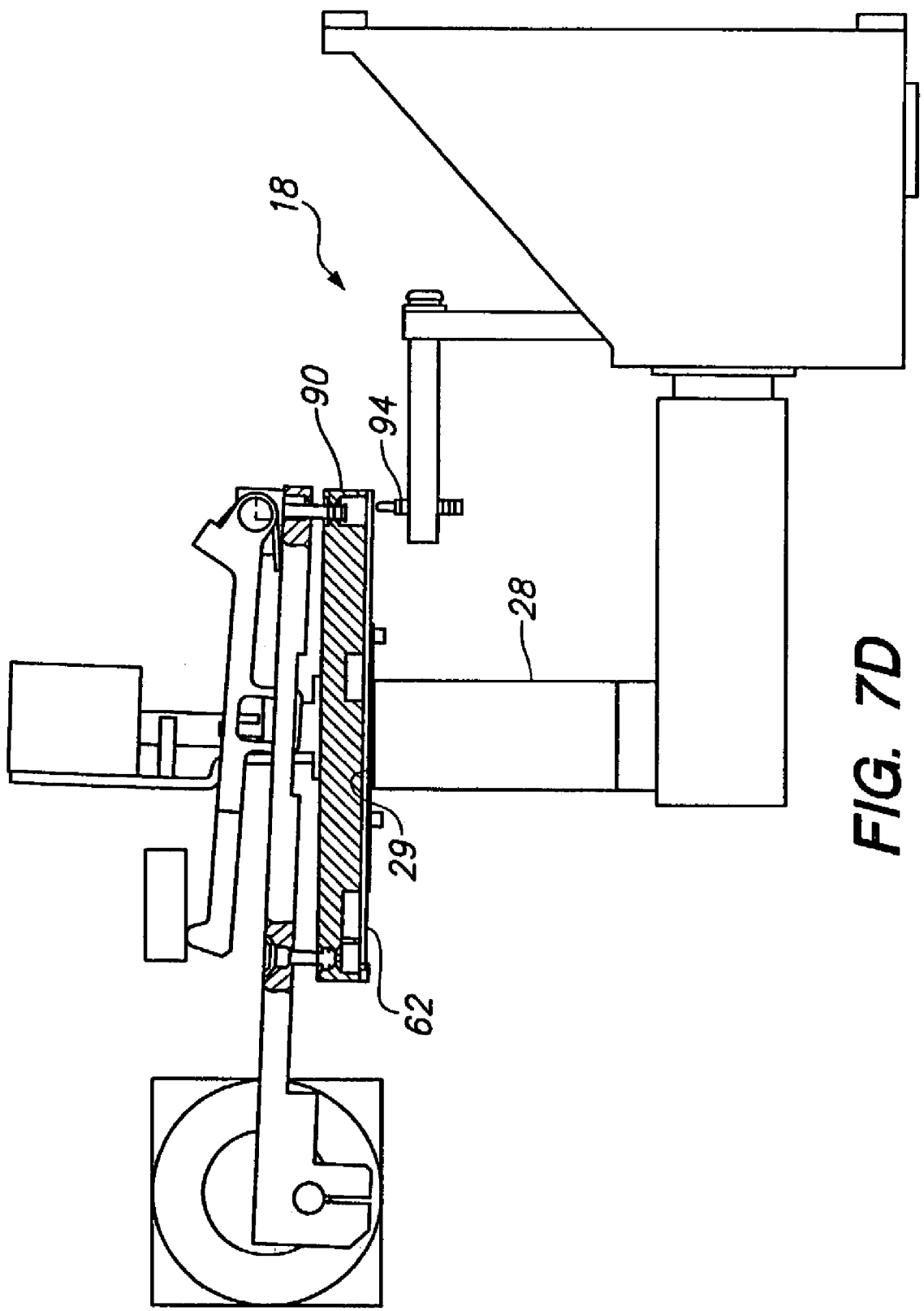
FIG. 7D is a schematic side view of a full contact condition of a sample collector contacting a specimen slide.

As the apparatus 18 is raised further to an end-of-travel position, as depicted in FIG. 7D, substantially full planar contact results between the membrane 29 and the slide 62, as the slide holder 90 is effectively fully supported by the membrane end of the collector 28. Note the clearance between the jack screws 94 and the holder 90 at the end-of-travel position. Accordingly, by initially providing a two point contact between the jack screws 94 and slide holder 90, the holder 90 and, as a result, the slide 62 mounted thereon, can be oriented in such a manner as to be nearly parallel to the collector membrane 29 when the membrane edge 29a first touches the slide. 62. As the apparatus 18 moves to the end-of-travel position, the slight rotation of the holder 90 through about one degree or so conforms the membrane 29 to the surface of the slide 62, gently displacing any excess liquid from the surface of the membrane and substantially preventing the capture of air bubbles between the membrane 29 and the slide 62 without disturbing the spatial distribution of the cells. With intimate contact now achieved between the membrane 29 and the slide 62, the cells captured therebetween can be readily transferred, for example with minimal positive pressurization of the collector 28 which slightly bows the membrane into a convex configuration.

As the membrane 29 is thereafter withdrawn from the surface of the slide 62, the reverse procedure takes place, leaving the transferred cells on the slide 62 in a undisturbed monolayer, substantially similar to the spatial distribution created when initially collected against the membrane 29. By providing clearance between the studs 92 and the slide holder 92 which affords a limited vertical range of motion of the slide holder 90, monolayers of cells can be reliable and repeatably transferred to slides 62 from a plurality of patient samples. Additionally, because the slide holder 90 is effectively floating at the time of cell transfer on a fluid bearing created at the interface of the membrane 29 and the slide 62, variability in slide thickness, membrane location, and slide/membrane parallelism are readily accommodated. Accordingly, there is no requirement for time consuming, precision setup of the apparatus 18 and slide holder 90 to ensure proper cell transfer.

After transferring the cells to the slide 62, a fixitive solution may then be applied to the transferred specimen and the slide 62 transferred from the slide carriage 64 to one of the staining racks 34 at the unloading area 36 using a slide transfer assembly such as a translating slide ejector 86. The slide ejector 86 and/or the unloading area 36 may include automatic height and side-to-side translation capability, so as to be able to accept the prepared specimen slide 62 in a next open slot in any one of the plurality of staining racks 34.

After preparation of the specimen, the membrane 29 of the used collector 28 is breached and the collector 28 discarded in the waste bin 44. The cap 56 is replaced on the sample vial 22a and the vial 22a returned to its location in the vial tray 24. If there exist additional sample vials 22 which have not yet been processed, a next vial 22 is removed automatically, the sample indicia identified, and a next specimen prepared therefrom according to the steps described hereinabove.

In order that the system can process automatically the specimens from fluid samples in the sample vials 22, each vial 22 and cap 56 includes one or more structural features which facilitate grasping of the closed, capped vial 22 by the sample vial transfer assembly 52, as well as removal and reinstallation of the cap 56. In one embodiment depicted in FIG. 5, the sample vial 22 includes a body 23 having a generally cylindrical outer surface, an open end, a closed end, and at least one lug 25 disposed about the outer surface. The lug 25 performs an anti-rotation function, preventing the body 23 from rotating when disposed against adjacent structure. The sample vial cap 56 is releasably engagable with the body 23, the cap 56 including an outer surface with a torque pattern 27 thereon for mating with a rotatable interface of the sample vial transfer assembly 52 as discussed more fully hereinbelow. A seal is disposed between the body 23 and the cap 56 so as to be capable of forming a substantially fluid-tight seal therebetween.

Instead of a single anti-rotation lug 25, the body 23 may include a plurality of lugs 25 disposed about a perimeter of the body 23, such as the six equi-spaced lugs 25 of the embodiment of FIG. 5. While the lugs 25 may be disposed anywhere on the body 23 accessible to the sample vial transfer assembly 52 or related structure of the system 10, the lugs 25 may be disposed advantageously proximate the open end of the body 23 and the cap 56. In this manner, torque may be applied to both the body 23 and the cap 56 at approximately the same axial plane to minimize any induced moment in the vial 22 during removal and installation of the cap 56.

The sample vial body 23 may be manufactured from a substantially transparent or translucent material so that a level of the fluid sample therein can be readily discerned by the system operator to ensure the presence of a sufficient amount of fluid for subsequent processing. The body 23 may also include fluid level indicia 31 disposed on the outer surface thereof, such as a circumferentially-disposed frosted annular band. Accordingly, the vials 22 can be rapidly visually screened by the operator prior to loading in the vial tray 24 to prevent loading a vial 22 with too much or too little fluid which might not be processed successfully by the specimen preparing apparatus 18. The fluid level indicia 31 may be provided in addition to the sample bar code label 58 discussed hereinabove.

The cap may be manufactured from polypropylene or other suitable material and may include knurling 33 or other anti-slip feature along an outer perimeter thereof to facilitate manual handling by a nurse or doctor during sample procurement, as well as the system operator during manual loading and loading of the sample vial trays 24. The cap torque pattern 27 may be at least one generally radially disposed rib 35. In the embodiment depicted in FIG. 5, the torque pattern 27 includes six generally radially disposed, equi-spaced ribs 35.

The seal may be manufactured from any suitable material which can be sterilized and which is capable of withstanding attack by the preservative fluid, which may typically contain a solution of methanol in a buffer. For example, the seal may be manufactured from a multicomposite material such as a resilient rubber layer laminated with a suitable vapor barrier and may be disposed within the cap 56. The cap 56 and the body 23 may have mating screw threads, a bayonet fitting, or other retention feature so as to be releasably engageable. In one embodiment, a substantially fluid-tight seal between the body 23 and the cap 56 may be formed when at least between about 5 and 50 inch-pounds of torque is applied to the cap 56 relative to the body 23. A more typical torque range may be on the order of about 20 to 30 inch-pounds, with about 25 inch-pounds being preferred. To ensure that the fluid-tight seal is produced when the patient's cells are first disposed in the preservative fluid and to prevent leakage or evaporation of the preservative fluid during transport and storage, each of the cap 56 and the body 23 may include alignment markers 37, 39, such that the alignment markers 37, 39 indicate a fluid-tight seal when at least aligned.

Figure 8:
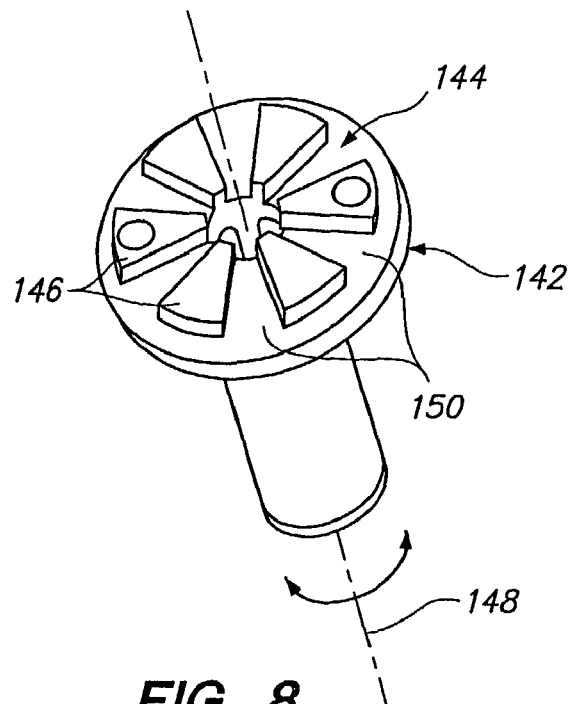
FIG. 8 is a schematic perspective view of a rotatable interface for mating with a torque pattern of a sample vial cap.

FIG. 8 is a schematic perspective view of one design of a rotatable interface 142 disposed radially inwardly of the grippers 54 of the vial transfer assembly 52. The interface 142 includes a torque pattern 144 for mating with the torque pattern 127 of the sample vial cap 56. The rotatable interface 142 is shown inverted, to better depict the interface torque pattern 144 formed therein. In this embodiment, the interface torque pattern 144 includes six raised wedge-shaped sectors 146. The sectors 146 are substantially equi-spaced about the interface 142, which is rotatable about a longitudinal axis 148 thereof, and sized to mate with the torque pattern 127 of the cap 56. Accordingly, the ribs 35 of the cap 56 fit in grooves 150 formed between the sectors 146 of the interface 142 and react against substantially vertical faces of the sectors 146 to permit both loosening and tightening of the cap 56.

Figure 9A:
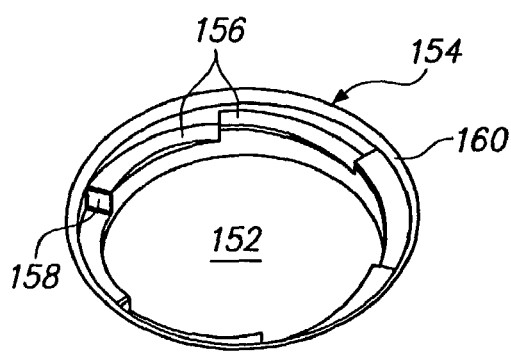
FIG. 9A is a schematic perspective view of a unidirectional interface in a sample vial tray for mating with anti-rotation features of a sample vial body.

To prevent rotation of the sample vial body 23 during these operations, the body 23 may be disposed in a bore 152 formed in the sample vial tray 24 having a unidirectional interface 154 along an edge 160 thereof for mating with the lugs 18 of the body 23, as depicted in FIG. 9A. The interface 154 includes six ramps 156, each including a substantially vertical face 158 which abuts one of the body lugs 25. Accordingly, the capped vial 22 may be disposed in the bore 152 with a flange 140 of the body 23 supported along the edge 160. The rotatable interface 142 may then be engaged with and tighten the cap 56, to ensure a fluid-tight seal prior to removing the vial 22 from the sample tray 24. Due to the orientation of the ramps 156, the lugs 25 react against the ramp faces 158 during tightening to positively secure and prevent rotation of the vial body 23.

Figure 9B:
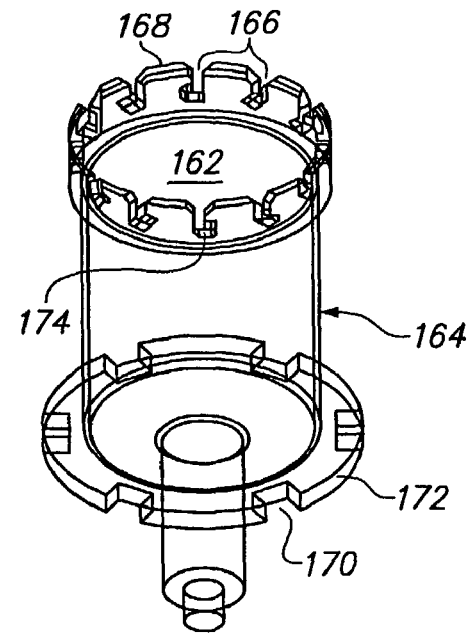
FIG. 9B is a schematic perspective view of a bidirectional interface for mating with anti-rotation features of a sample vial body.

Once the cap 56 has been tightened, the vial transfer assembly 52 may grasp the capped vial 22 about the circumference of the cap 56 with the grippers 54, remove the vial 22 from the bore 152 in the tray 24, rotate the vial 22 in front of the bar code reader 60, and deposit the capped vial 22 in a bore 162 formed in a vial sleeve 164, such as that depicted in FIG. 9B in wire form representation. The six lugs 25 of the capped vial 22 are received in every other one of twelve axially extending slots 166 formed along an upper edge 168 of the sleeve 164, the flange 140 of the vial 22 being supported by the edge 168. Once in the bore 162 with the lugs 25 disposed in the slots 166, further processing may proceed.

As discussed hereinabove, a slide 62 is printed and the slide indicia 82 verified as being readable and corresponding to the vial bar code label 58. The vial 22 may then be uncapped and the sample collector 28 can be disposed in the vial 22 and rotated to disperse the cells in the sample. According to an alternative embodiment, once the capped vial 22 is disposed in the sleeve 164 and before the vial 22 is uncapped, the sleeve 164 may be rotated in one or both directions to disperse the cells in the preservative solution. Thereafter, a pin, clamp, or other structural feature of the system 10 may engage one of a series of notches 170 formed in a flange 172 of the sleeve 164 to prevent rotation of the sleeve 164 and the vial 22 disposed therein while the rotatable interface 142 engages and unscrews the cap 56. The cap 56 is then retracted by the gripper 54 of the vial transfer assembly 52 and the sample collector 28 disposed in the preservative solution in the vial 22 to collect the cells against the filter 29 thereof and thereafter transfer the cells to the slide 62. Once the cytological specimen has been prepared, the cap 56 is reoriented over the open vial 22 and screwed onto the body 23 until a substantially fluid-tight seal has been formed. The axially extending slots 166 which engage the lugs 25 form a bi-directional interface, to react against the body lugs 25 during both removal and installation of the cap 56 on the body 23. Each of the axial slots 166 may be formed to include, optionally, a generally circumferentially disposed portion, shown generally at 174, to lock a suitably sized lug against axial translation, if desired.

Of course, other suitable materials, dimensions, and configurations for the body 23, the cap 56, the ribs 35, the lugs 25, the fluid level indicia 31, and other features of the sample vial 22 will be apparent to those skilled in the art, those disclosed being provided as examples only. For example, while the mating ribs 35 and sectors 146 provide a positive, self-centering drive, other mating structure such as pins and annular tracks may be used. Further, the sample vial 22 may be used in other applications and contain other than cytological samples in preservative solution.

The automated specimen preparing system 10 described herein employs certain specimen preparing innovations disclosed in the aforementioned patents in combination with batch processing capability to prepare gynecological and other cytological specimens in a highly efficient, reliable manner. The system 10 may also be used to batch process other specimens such as those including tissue samples, assay products, and other materials. Industry and regulatory acceptance of a system 10 and method in accordance with the teachings set forth herein are based, in part, on the capability to maintain one-to-one correlation between a patient sample and a specimen produced therefrom. Accordingly, a specimen is not produced on an unmarked slide 62, or on a slide 62 on which the specimen indicia are not readable or do not correlate with the sample indicia bar code label 58 identified from the selected vial 22a. By aborting the specimen preparing cycle prior to collection of the cells against the membrane 29, unidentifiable or misidentified specimen slides are not produced, saving cycle time, consumables, and the patient's sample.

When a patient's cells are first collected and deposited in a sample vial 22 prefilled with preservative solution, a preprinted bar code label 58 with a unique accession number is applied to the sample vial 22. A second matching bar code label 58 is applied to a patient information sheet, listing relevant patient identifying information, as well as information regarding the tests or analyses to be performed on the specimen prepared from the sample. Accordingly, when data from the patient information sheet is entered into a database at a sample receiving area in a cytological laboratory, data from the bar code label 58 on the patient information sheet can also be input, either manually or preferably automatically using a laser scanner. The specimen produced from the sample with the matching bar code will therefore readily be identifiable as being from a particular patient.

Once the system 10 is loaded with the samples and consumables by the operator, the system 10 runs in an automated manner under control of the processor 46 until all sample vials 22 are processed, or until such time as a system malfunction occurs or a consumable, such as a sample collector 28 or slide 62, is depleted. To minimize the likelihood of the latter situation, sensors are provided throughout the system 10 to verify the presence of sufficient consumables to process all loaded samples prior to the initiation of automatic operation. Sensors may also be provided to monitor levels in the waste bottle 42 and waste bin 44, so that the operator can be alerted to elevated levels of waste, which could interrupt processing during automatic cycling.

Accordingly, when the operator initiates automatic processing, for example, by selecting "Start Batch" from a menu on the display or using a dedicated keypad input, the system 10 checks that sample vials 22 are loaded and a minimum number of necessary consumables and staining racks are available to complete processing of all the samples. If sufficient consumables and waste capacities exist, the system 10 starts the automatic sample processing cycle. The cycle continues until all of the loaded sample vials 22 have been processed, the operator manually interrupts the cycle, or a system error occurs which cannot be automatically rectified. If insufficient consumables or waste capacities exist, the operator may correct the condition or, alternatively, override the system 10 and initiate automatic processing anyway. In the event a prior automatic cycle had been interrupted, "Start Batch" may be used to resume automatic cycling at the point of interruption, after checking system consumables and capacities. In order to protect the operator from injury by moving components during automatic cycling, access points such as the upper cover 14 may be interlocked.

If the operator chooses to interrupt the automatic cycle prior to completion, the operator may select "Interrupt Batch." Upon receipt of the interrupt signal, the processor 46 interrupts the automatic cycle in an orderly manner, for example, by completing preparation of a specimen in process, transferring the completed specimen slide 62 to a staining rack 34 in the unloading area 36, and capping and returning the selected sample vial 22a to the vial tray 24. After that sample processing cycle has been completed and moving components are at rest at respective home positions, the operator access interlocks are unlatched and the operator is notified. The operator may then open the upper cover 14 or access other internal areas of the system 10, as desired.

A "Maintenance" function can also be provided in which the system 10 supports operator level maintenance activities such as jogging of the moving components to or from respective home positions to provide the operator access to various interior volumes of the system 10, for example, to clear a jam or to retrieve a mishandled slide 62. Other maintenance functions may include emptying of the waste bottle 42 and bin 44, priming of the fixitive coating station 38 with the fixitive solution, and advancing of paper in the system printer 48. The system 10 may also provide operator selectable diagnostic tests to facilitate system troubleshooting or verify proper system operation. For example, a pneumatic test may be initiated of the vacuum system 88 of the specimen preparing apparatus 18 to ensure sufficient volumetric flow rate and negative pressure level. A display test could be used to verify display operation.

A usage log may be provided to track total number of samples processed, total number of specimens produced, total system run time, and other relevant usage parameters. The processor 46 may also maintain an error log which lists, for example, the last fifty errors detected by the system 10 and which may be displayed or printed at the discretion of the operator. A typical log entry may include date and time of the error, sample indicia and tray location, and disposition or corrective action. In one embodiment, the system 10 identifies any sample vial 22 from which a specimen was not successfully prepared, along with the reason for the failure, such as "sample too dense" or "cap too tight."

Detectable conditions that could cause specimen quality problems are flagged by the system 10 and noted to the operator on the display and paper printout. If possible, a partially collected specimen is returned to the vial 22 and preparation of the slide 62 is aborted. If the problem is associated with a particular selected sample vial 22a, the system 10 recovers after returning the selected vial 22a to the vial tray 24 and recording the error, processing the remaining sample vials 22 in the batch. However, if the error is a system level problem, such as a motor or sensor failure, jammed mechanism, or other malfunction that is not automatically recoverable and requires operator or qualified service personnel intervention, the automatic cycle is halted and the error recorded and reported to the operator.

Upon installation or commissioning of the system 10, or thereafter as required, the processor 46 may be initialized and setup functions enabled or disabled. For example, the date and time may be input, as well as the respective formats thereof. The system printer 48 may be directed to automatically print diagnostic test results or sample processing data at the end of every automatic batch cycle. A date/time stamp may be enabled to print the date and time a specimen was prepared on the frosted end 68 of each slide 62, in addition to the slide indicia 82. Optionally, the name or other identifier of the cytological laboratory preparing the specimen with the system 10 may be printed on the slide 62 as well.

While there have been described herein what are to be considered exemplary and preferred embodiments of the present invention, other modifications of the invention will become apparent to those skilled in the art from the teachings herein. For example, while the system 10 and method have been described for preparing a single specimen from each sample vial 22, the system 10 could be programmed to permit two or more specimens to be prepared from a single sample vial 22. In such instances, the slide indicia 82 could include an additional character or identifier to indicate the first specimen, second specimen, third specimen, etc. Alternatively, the sample vial 22 could be reprocessed by inserting the vial 22 in a tray 24 in a next batch for a subsequent automatic cycle.

The disclosed components of the system 10 may be manufactured in various sizes, configurations, and materials. Additionally, the system 10 may be used to prepare specimens from non-gynecologic cytological samples, such as cells sourced from fine needle aspirates, from mucoid specimens taken from respiratory and gastrointestinal tracts, from body fluids such as serous effusions and urinary and cerebrospinal fluids, from superficial brushings and scrapings from oral cavities, nipple secretions, skin lesions, and eye brushings, and from other sources.

The particular methods of manufacture and particular arrangements of discrete components, geometries, and interconnections therebetween disclosed herein are exemplary in nature and are not to be considered limiting. It is therefore desired to be secured in the appended claims all such modifications as fall within the spirit and scope of the invention. Accordingly, what is desired to be secured by Letters Patent is the invention as defined and differentiated in the following claims.

What is claimed is:

1. A method for preparing a plurality of specimens from a plurality of fluid samples, the method comprising the steps of:
   (a) loading a plurality of samples into a location of a first loading station;
   (b) removing an individual first sample from the first loading station;
   (c) preparing a first specimen from the individual first sample;
   (d) returning the individual first sample to the location of the first loading station;
   (e) transferring the first specimen to an unloading area separate from the first loading station, wherein the location of the first loading station is fixed relative to the unloading area; and
   (f) repeating steps (b) through (e) with remaining ones of the plurality of samples to prepare subsequent specimens until all of the plurality of samples have been processed.

2. A method according to claim 1 further comprising the step of maintaining correlation between each one of the plurality of samples and a respective specimen prepared therefrom.

3. A method according to claim 2 wherein the correlation maintaining step comprises the substeps of:
   identifying indicia corresponding to the first sample;
   marking a first analytical element with indicia corresponding to the first sample indicia;
   reading the first element indicia;
   verifying the first element indicia corresponds to the first sample indicia;
   transferring the first specimen from the individual first sample to the first analytical element if the first element indicia corresponds to the first sample indicia; and
   repeating the substeps with remaining ones of the plurality of samples to maintain correlation with subsequent respective specimens prepared therefrom.

4. A method according to claim 1 wherein repeating steps (b) through (e) with remaining ones of the plurality of samples commences prior to completion of steps (b) through (e) with the first sample.

5. A method according to claim 1 wherein the specimen preparing step comprises collecting a spatial distribution of particles and disposing the collected particles on a stratum of an analytical element.

6. A method according to claim 5 wherein the particles comprise cells.

7. A method according to claim 5 further comprising the step of coating each prepared specimen with a fixative solution.

8. A method according to claim 5 wherein the spatial distribution comprises substantially a monolayer and the stratum comprises a slide.

9. A method according to claim 5 wherein the spatial distribution of particles is collected using a membrane.

10. A method according to claim 1 wherein the first specimen is unconditionally prepared from the first sample.

11. A method according to claim 1 wherein the individual first sample is removed from a location at the first loading station and returned to the same location at the first loading station.

12. A method according to claim 1 further comprising the steps of:
    loading a plurality of sample collectors into a second loading station;
    removing an individual first sample collector from the second loading station to prepare the first specimen from the individual first sample;
    discarding the individual first sample collector after preparing the first specimen; and
    repeating the sample collector removing step and the sample collector discarding step with remaining ones of the plurality of samples to prepare subsequent specimens until all of the plurality of samples have been processed.

13. A method according to claim 12 wherein each of the sample collectors comprises a membrane.

14. A method according to claim 13 further comprising the steps of:
    breaching the individual first membrane after preparing the first specimen to prevent reuse of the first membrane; and
    repeating the membrane breaching step with remaining ones of the plurality of membranes until all of the plurality of samples have been processed.

15. A method according to claim 1 further comprising placing the plurality of samples within a tray, wherein loading the plurality of samples into the first loading station comprises placing the tray into the first loading station, and wherein the individual first sample is returned to the tray at the first loading station.

16. A method according to claim 1 wherein the plurality of samples is manually loaded into the first loading station.

17. A method for preparing a plurality of specimens from a plurality of fluid samples, the method comprising:
    (a) loading a plurality of samples into a first loading station;
    (b) removing an individual first sample from the first loading station;
    (c) unconditionally preparing a first specimen from the individual first sample during normal operation;
    (d) returning the individual first sample to the first loading station;
    (e) transferring the first specimen to an unloading area separate from the first loading station; and (f) repeating steps (b) through (e) with remaining ones of the plurality of samples to prepare subsequent specimens until all of the plurality of samples have been processed.

18. A method according to claim 17 wherein the specimen preparing step comprises collecting a spatial distribution of particles and disposing the collected particles on a stratum of an analytical element.

19. A method according to claim 17 wherein repeating steps (b) through (e) with remaining ones of the plurality of samples commences prior to completion of steps (b) through (d) with the first sample.

20. A method according to claim 17 further comprising the steps of:
- loading a plurality of sample collectors into a second loading station;
- removing an individual first sample collector from the second loading station to prepare the first specimen from the individual first sample;
- discarding the individual first sample collector after preparing the first specimen; and
- repeating the sample collector removing step and the sample collector discarding step with remaining ones of the plurality of samples to prepare subsequent specimens until all of the plurality of samples have been processed.

21. A method according to claim 20 wherein each of the sample collectors comprise a membrane.

22. A method according to claim 21 further comprising the steps of:
- breaching the individual first membrane after preparing the first specimen to prevent reuse of the first membrane; and
- repeating the membrane breaching step with remaining ones of the plurality of membranes until all of the plurality of samples have been processed.

23. A method for preparing a plurality of specimens from a plurality of fluid samples, the method comprising:
(a) loading a plurality of samples into a first loading station;
(b) loading a plurality of sample collectors into a second loading station;
(c) removing an individual first sample from the first loading station;
(d) removing an individual first sample collector from the second loading station to take the first specimen from the individual first sample;
(e) preparing a first specimen from the individual first sample using the individual first sample collector;
(f) returning the individual first sample to the first loading station;
(g) discarding the individual first sample collector after preparing the first specimen;
(h) transferring the first specimen to an unloading area; and
(i) repeating steps (b) through (h) with remaining ones of the plurality of samples to prepare subsequent specimens until all of the plurality of samples have been processed.

24. A method according to claim 22 wherein the samples are carried in a plurality of respective containers, the method further comprising placing the removed first specimen on a stratum of an analytical element.

25. A method according to claim 22 wherein each of the sample collectors comprise a membrane.

26. A method according to claim 22 wherein repeating steps (b) through (h) with remaining ones of the plurality of samples commences prior to completion of steps (b) through (h) with the first sample.

27. A method according to claim 22 wherein the first specimen is unconditionally taken from the first sample.

28. A method according to claim 22 further comprising the steps of:
- breaching the individual first membrane after preparing the first specimen to prevent reuse of the first membrane; and
- repeating the membrane breaching step with remaining ones of the plurality of membranes until all of the plurality of samples have been processed.

* * * * *